US008568464B2

(12) United States Patent
Dae et al.

(10) Patent No.: US 8,568,464 B2
(45) Date of Patent: *Oct. 29, 2013

(54) METHOD FOR REDUCING MYOCARDIAL INFARCT BY APPLICATION OF INTRAVASCULAR HYPOTHERMIA

(75) Inventors: Michael W. Dae, Belmont, CA (US);
Wade A. Keller, San Jose, CA (US);
Timothy R. Machold, Moss Beach, CA (US)

(73) Assignee: ZOLL Circulation, Inc., Sunnyvale, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 12/415,984

(22) Filed: Mar. 31, 2009

(65) Prior Publication Data
US 2009/0254161 A1      Oct. 8, 2009

Related U.S. Application Data

(63) Continuation of application No. 10/933,979, filed on Sep. 2, 2004, now Pat. No. 7,510,569, which is a continuation of application No. 09/735,314, filed on Dec. 12, 2000, now Pat. No. 6,811,551.

(60) Provisional application No. 60/170,831, filed on Dec. 14, 1999.

(51) Int. Cl.
    *A61F 7/12*      (2006.01)
(52) U.S. Cl.
    USPC .......................................................... 607/105
(58) Field of Classification Search
    USPC .......................................................... 607/105
    See application file for complete search history.

(56) References Cited

U.S. PATENT DOCUMENTS

| 3,007,473 | A | * | 11/1961 | Jackson et al. ................ 607/104 |
| 3,064,649 | A | * | 11/1962 | Fuson ............................. 96/205 |
| 3,425,419 | A |   | 2/1969  | Dato |
| 4,581,017 | A | * | 4/1986  | Sahota ...................... 604/101.01 |
| 5,182,106 | A | * | 1/1993  | Mezrow et al. ............. 424/78.31 |
| 5,486,208 | A |   | 1/1996  | Ginsgurg |
| 5,534,504 | A | * | 7/1996  | Sollevi ............................. 514/46 |
| 5,624,392 | A |   | 4/1997  | Saab |
| 5,655,548 | A | * | 8/1997  | Nelson et al. ................. 128/898 |
| 5,676,670 | A | * | 10/1997 | Kim ............................. 606/108 |

(Continued)

OTHER PUBLICATIONS

International Search Report in reference to PCT/US00/42749, International Searching Authority, Jun. 1, 2001.

*Primary Examiner* — Linda Dvorak
*Assistant Examiner* — Kaitlyn Smith
(74) *Attorney, Agent, or Firm* — Robert D. Buyan; Stout, Uxa, Buyan & Mullins, LLP

(57) ABSTRACT

Methods and apparatus for preventing myocardial infarction, or lessening the size/severity of an evolving myocardial infarction, by cooling at least the affected area of the myocardium using an intravascular heat exchange catheter. The heat exchange catheter may be inserted into the vasculature (e.g., a vein) and advanced to a position wherein a heat exchanger on the catheter is located in or near the heart (e.g., within the vena cava near the patient's heart). Thereafter, the heat exchange catheter is used to cool the myocardium (or the entire body of the patient) to a temperature that effectively lessens the metabolic rate and/or oxygen consumption of the ischemic myocardial cells or otherwise protects the ischemic myocardium from undergoing irreversible damage or infarction.

24 Claims, 12 Drawing Sheets

(56) References Cited

U.S. PATENT DOCUMENTS

| | | | |
|---|---|---|---|
| 5,695,457 A * | 12/1997 | St. Goar et al. | 604/4.01 |
| 5,730,720 A * | 3/1998 | Sites et al. | 604/27 |
| 5,797,920 A * | 8/1998 | Kim | 606/108 |
| 5,799,661 A * | 9/1998 | Boyd et al. | 128/898 |
| 5,837,003 A * | 11/1998 | Ginsburg | 607/106 |
| 5,957,963 A | 9/1999 | Dobak, III | |
| 5,980,548 A * | 11/1999 | Evans et al. | 606/185 |
| 6,007,544 A * | 12/1999 | Kim | 606/108 |
| 6,042,559 A | 3/2000 | Dobak, III | |
| 6,051,019 A * | 4/2000 | Dobak, III | 607/104 |
| 6,090,132 A * | 7/2000 | Fox | 607/96 |
| 6,101,412 A * | 8/2000 | Duhaylongsod | 607/2 |
| 6,110,168 A | 8/2000 | Ginsburg | |
| 6,113,621 A * | 9/2000 | Wiktor | 606/195 |
| 6,127,410 A * | 10/2000 | Duhaylongsod | 514/478 |
| 6,149,676 A | 11/2000 | Ginsburg | |
| 6,161,547 A * | 12/2000 | Barbut | 128/898 |
| 6,165,199 A * | 12/2000 | Barbut | 606/200 |
| 6,167,885 B1 * | 1/2001 | Hanssen | 128/849 |
| 6,203,556 B1 * | 3/2001 | Evans et al. | 606/185 |
| 6,231,551 B1 * | 5/2001 | Barbut | 604/236 |
| 6,231,594 B1 | 5/2001 | Dae | |
| 6,235,048 B1 * | 5/2001 | Dobak, III | 607/104 |
| 6,238,428 B1 | 5/2001 | Werneth et al. | |
| 6,264,679 B1 | 7/2001 | Keller et al. | |
| 6,266,551 B1 * | 7/2001 | Osadchy et al. | 600/424 |
| 6,287,326 B1 | 9/2001 | Pecor | |
| 6,290,717 B1 | 9/2001 | Philips | |
| 6,299,599 B1 | 10/2001 | Pham et al. | |
| 6,312,452 B1 | 11/2001 | Dobak, III et al. | |
| 6,325,818 B1 | 12/2001 | Werneth | |
| 6,338,727 B1 | 1/2002 | Noda et al. | |
| 6,368,304 B1 * | 4/2002 | Aliberto et al. | 604/113 |
| 6,393,320 B2 | 5/2002 | Lasersohn et al. | |
| 6,414,018 B1 * | 7/2002 | Duhaylongsod | 514/478 |
| 6,428,563 B1 * | 8/2002 | Keller | 607/105 |
| 6,432,124 B1 * | 8/2002 | Worthen et al. | 607/105 |
| 6,482,226 B1 * | 11/2002 | Dobak, III | 607/104 |
| 6,544,282 B1 * | 4/2003 | Dae et al. | 607/105 |
| 6,554,797 B1 * | 4/2003 | Worthen | 604/113 |
| 6,582,398 B1 * | 6/2003 | Worthen et al. | 604/113 |
| 6,585,692 B1 * | 7/2003 | Worthen | 604/113 |
| 6,673,040 B1 * | 1/2004 | Samson et al. | 604/101.01 |
| 6,709,427 B1 * | 3/2004 | Nash et al. | 604/508 |
| 6,716,188 B2 | 4/2004 | Noda et al. | |
| 6,716,236 B1 * | 4/2004 | Tzeng et al. | 607/105 |
| 6,752,786 B2 * | 6/2004 | Callister | 604/113 |
| 6,843,800 B1 * | 1/2005 | Dobak, III | 607/105 |
| 7,083,588 B1 * | 8/2006 | Shmulewitz et al. | 604/8 |
| 8,317,491 B2 * | 11/2012 | Noda et al. | 417/360 |
| 2001/0005791 A1 * | 6/2001 | Ginsburg et al. | 607/106 |
| 2001/0008969 A1 * | 7/2001 | Evans et al. | 606/185 |
| 2001/0027287 A1 * | 10/2001 | Shmulewitz et al. | 604/7 |
| 2001/0041923 A1 * | 11/2001 | Dobak, III | 607/108 |
| 2002/0022823 A1 | 2/2002 | Luo et al. | |
| 2002/0056460 A1 * | 5/2002 | Boyd et al. | 128/898 |
| 2002/0066458 A1 * | 6/2002 | Aliberto et al. | 128/898 |
| 2002/0111616 A1 * | 8/2002 | Dea et al. | 606/41 |
| 2002/0151946 A1 * | 10/2002 | Dobak, III | 607/105 |
| 2002/0193738 A1 * | 12/2002 | Adzich et al. | 604/113 |
| 2002/0198578 A1 * | 12/2002 | Dobak, III | 607/104 |
| 2003/0045917 A1 * | 3/2003 | Noda et al. | 607/105 |
| 2003/0060761 A1 * | 3/2003 | Evans et al. | 604/113 |
| 2003/0083617 A1 * | 5/2003 | St. Germain et al. | 604/104 |
| 2003/0120210 A1 * | 6/2003 | Worthen et al. | 604/113 |
| 2003/0131844 A1 * | 7/2003 | Kumar et al. | 128/200.24 |
| 2003/0191449 A1 * | 10/2003 | Nash et al. | 604/523 |
| 2003/0195465 A1 * | 10/2003 | Worthen | 604/113 |
| 2005/0004636 A1 * | 1/2005 | Noda et al. | 607/105 |
| 2005/0027281 A1 * | 2/2005 | Lennox | 604/508 |
| 2006/0041217 A1 * | 2/2006 | Halperin et al. | 604/6.13 |
| 2006/0293734 A1 * | 12/2006 | Scott et al. | 607/105 |
| 2007/0043409 A1 * | 2/2007 | Brian et al. | 607/105 |
| 2007/0191918 A1 * | 8/2007 | MacHold et al. | 607/105 |
| 2007/0244434 A1 * | 10/2007 | Noda et al. | 604/113 |
| 2008/0091253 A1 * | 4/2008 | Hammack et al. | 607/106 |
| 2008/0119757 A1 * | 5/2008 | Winter | 600/549 |
| 2008/0119788 A1 * | 5/2008 | Winter | 604/113 |
| 2010/0137951 A1 * | 6/2010 | Lennox et al. | 607/104 |
| 2011/0137248 A1 * | 6/2011 | Winter | 604/113 |
| 2011/0208276 A1 * | 8/2011 | Machold et al. | 607/104 |
| 2011/0208277 A1 * | 8/2011 | Machold et al. | 607/104 |
| 2012/0325426 A1 * | 12/2012 | Noda et al. | 165/11.1 |

* cited by examiner

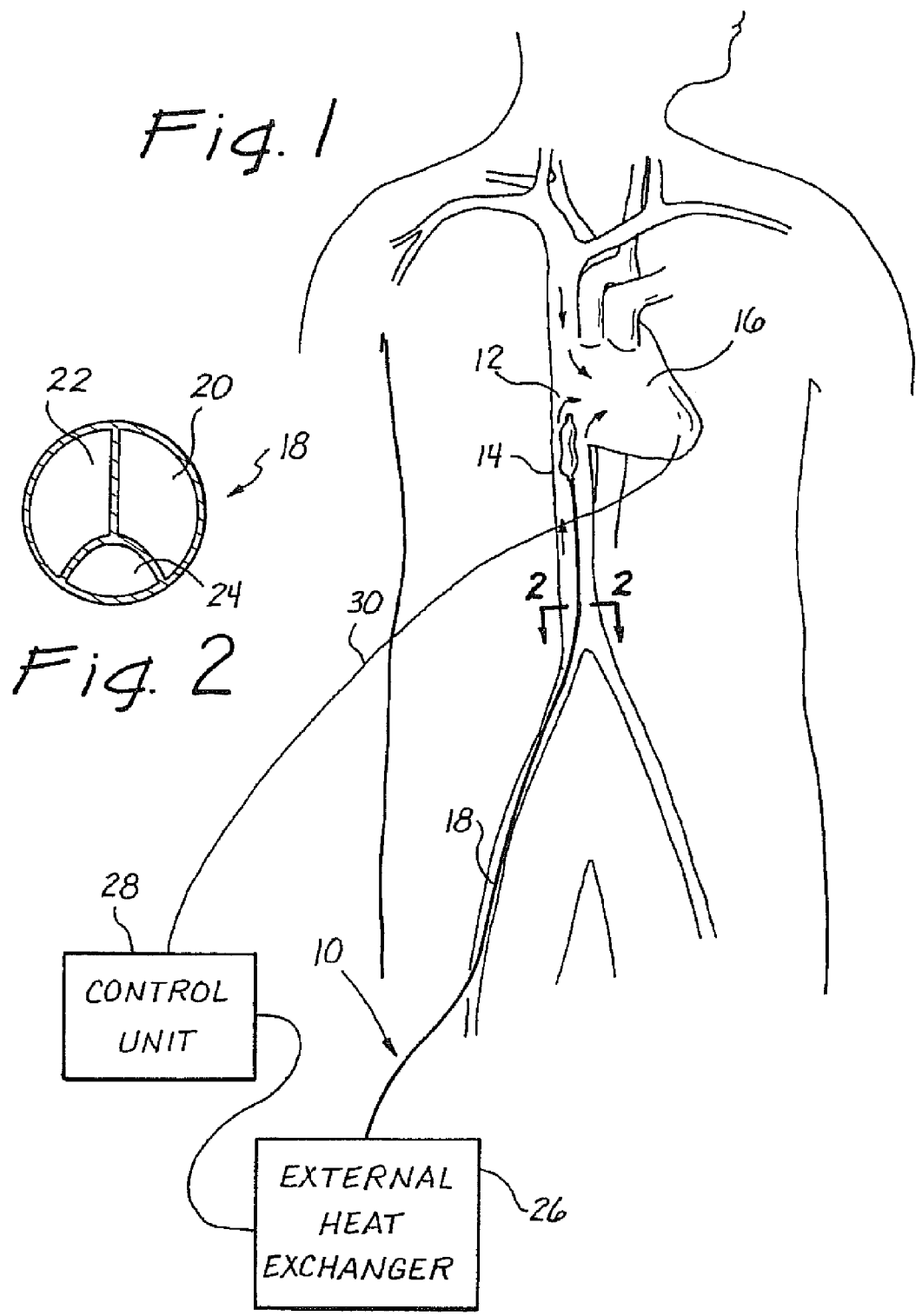

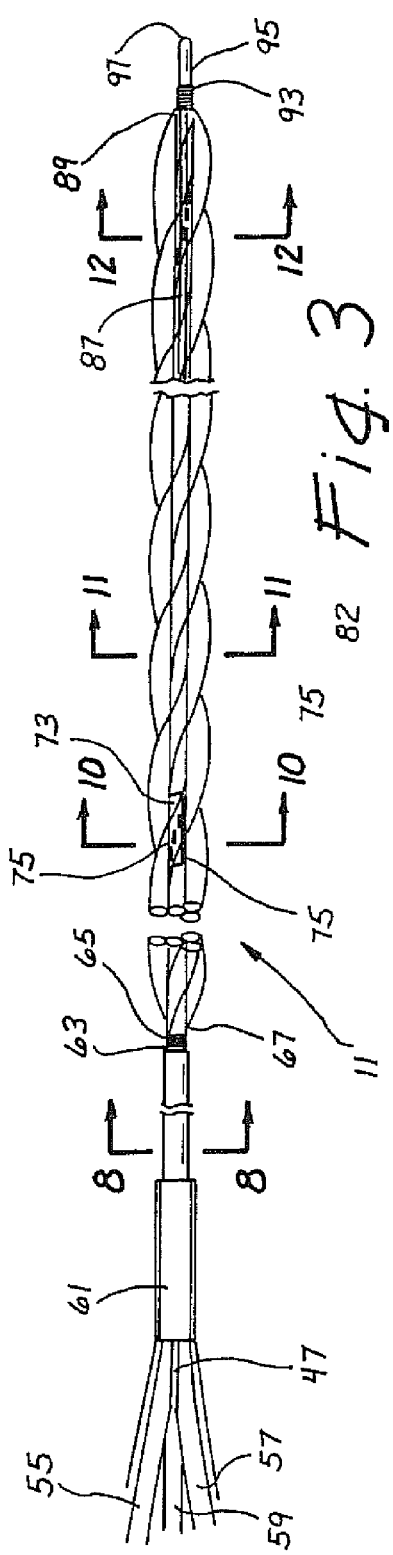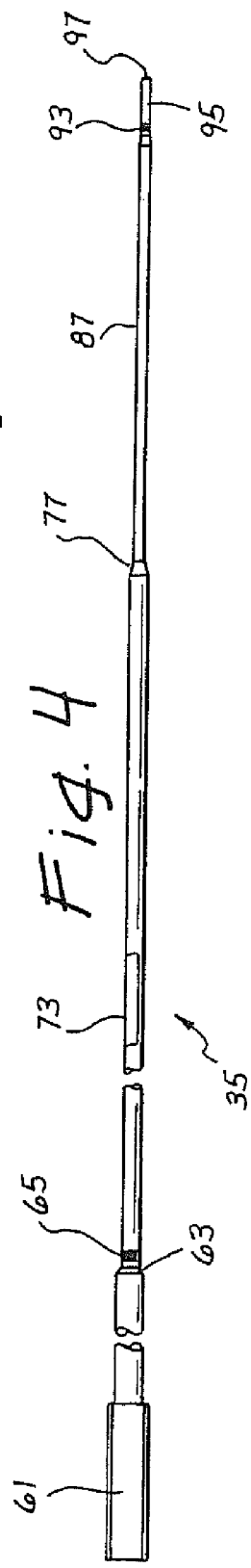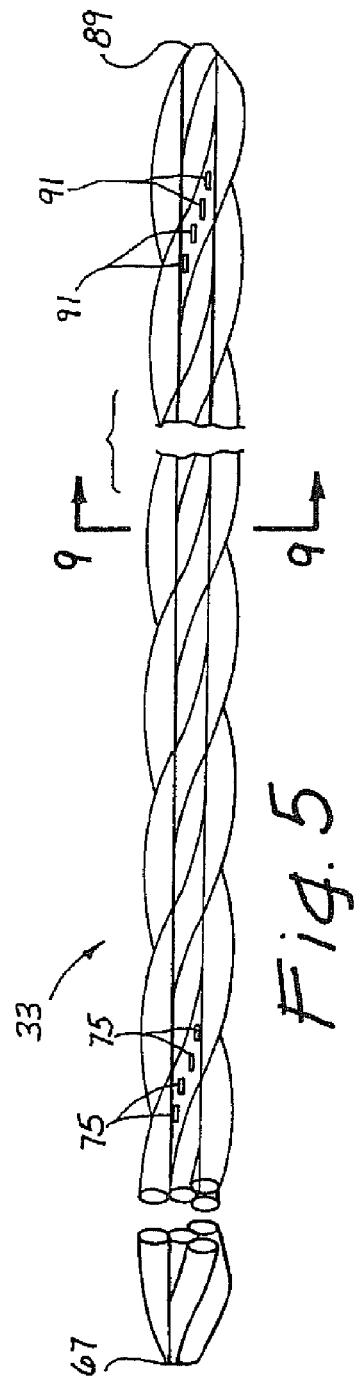

METHOD FOR REDUCING MYOCARDIAL INFARCT BY APPLICATION OF INTRAVASCULAR HYPOTHERMIA

RELATED APPLICATIONS

This application is a continuation of U.S. patent application Ser. No. 10/933,979 filed Sep. 2, 2004 now U.S. Pat. No. 7,510,569, which is a continuation of U.S. patent application Ser. No. 09/735,314 filed Dec. 12, 2000 now U.S. Pat. No. 6,811,551, which claims priority to U.S. Provisional Patent Application Ser. No. 60/170,831 filed Dec. 14, 1999, the entire disclosure of each such application being expressly incorporated herein by reference.

FIELD OF THE INVENTION

This invention relates generally to the field of cardiac therapy, and more particularly to the intravascular application of hypothermia to prevent or reduce myocardial infarct resulting from myocardial ischemia.

BACKGROUND OF THE INVENTION

When the normal blood supply a person's heart muscle is disrupted, the person may suffer what is commonly termed a heart attack. Heart attacks are one of the major health problems in the world. In the United States alone there are over 1.1 million heart attacks a year. Of those 1.1 million victims, about 250,000 die within 1 hour. However, those that survive the initial heart attack generally subsequently receive treatment. In fact, about 375,000 of those heart attack victims will make it to a hospital for treatment within 1 hour; about 637,000 will make it to a hospital for treatment within 4 hours. Unfortunately, when treated using current methods, heart attacks often result in serious and permanent damage to the heart muscle. In fact, it is estimated that about 66% of the MI patients do not make a complete recovery, but rather suffer permanent injury to cardiac muscle cells. An effective treatment that minimizes permanent damage to the heart as a result of the heart attack would be of great value to these patents.

In a typical heart attack, there is a blockage in an artery that provide blood to some of the cardiac muscle cells, so the cells in the affected portion of the heart (termed the area at risk) experience ischemia, or a lack of adequate blood flow. This ischemia results in an inadequate supply of oxygen for the muscles and inadequate removal of waste product of muscle activity such as $CO_2$, lactic acid or other by-products of metabolism. These substances may therefore reach toxic concentrations and thus, in turn, cause serious long-term consequences such as the breakdown of the cell walls, release of toxic enzymes or the like, and ultimately result in the death of many or all of the cardiac muscle cells in the area at risk.

The ischemia, however, is not always permanent. In fact, if the heart attack does not result in the immediate death of the individual, the ischemia is generally reversed either spontaneously or with medical intervention. If the ischemia is a result of blockage of an artery by a blood clot, the clot may spontaneously dissolve in the ordinary course of time due to the body's own natural thrombolytics, and blood may again flow to the affected area Alternatively, medical treatment may restore blood flow. Such medical treatments include administration of thrombolytic drugs, such as tPA, to dissolve blood clots in the vessels of the heart to restore blood flow, balloon angioplasty, where an interventional cardiologist steers a catheter with a balloon on the end into the clogged artery and inflates the balloon to open the artery, coronary stenting, where an interventional cardiologist steers a catheter with a stent on it into the clogged vessel and expands the stent to place what amounts to a scaffold into the vessel with the blockage to hold the vessel open, or coronary by-pass surgery where a blood vessel is harvested from elsewhere in the patient's body and is attached around a blocked coronary artery to restore blood to the ischemic tissue distal of the blockage. These treatments may be applied individually or in concert with one or more of the other treatments.

Generally if the ischemic event is for a short period of time or oxygenated blood is available to the affected tissue from another blood supply, for example from collateral arteries or even from blood within the heart cavity, some or all of the muscle cells in the area at risk may survive and ultimately recover much or all of their function. However, if the period of ischemia is long enough and severe enough, the cardiac muscle cells in the area at risk may in fact die as a result of the ischemic insult. The area of dead tissue resulting from this cell death is called an infarct and the area may be said to be infarcted.

Unlike many cells in the body, for example, skeletal muscle cells, cardiac muscle cells do not significantly regenerate. Thus an infarcted region of cardiac muscle cells will generally be a permanently non-functioning portion of the patient's heart. This will result in decreased overall heart function, which may lead to systemic vascular insufficiency, congestive heart failure, and even death. It is thus of great importance to minimize the amount of infarct that results from cardiac ischemic events.

Infarct may result from heart attacks as described above, and may also result from myocardial ischemic events as the result of other causes and may even be predicable. For example, in so-called beating heart by-pass surgery, the surgeon stops the heart for short periods of time to sew grafts onto the surface of the heart. In such a procedure, the heart is deprived of blood during the time that circulation is stopped, and unless protected, infarct can result from this ischemic event.

Another common interventional procedure, cardiac balloon angioplasty, also disrupts the blood supply to part of the heart and results in predictable ischemia. In balloon angioplasty of the heart, an interventional cardiologist inserts a balloon catheter into the vasculature of the heart with the balloon deflated. The balloon is placed at a location where the interventionalist wants to dilate the vessel, and then inflates the balloon against the walls of the vessel. When the balloon is inflated, it fills the vessel in question and blocks most if not all blood from flowing through that vessel. In this way, it creates an area of ischemia downstream from the balloon, which ischemia persists for as long as the balloon is inflated. Although attempts have been made to relieve this ischemia by means of catheters that allow perfusion from one side of the balloon to the other during inflation (so called auto-perfusion balloons), these have generally proven to be inadequate.

It is also sometimes the case that during or after angioplasty the dilated vessel is either dissected or goes into spasm. If the vessel spasms shut or is dissected, the blood supply to all the tissue vascularized by the artery in question suffers severe ischemia and potential infarct. In such cases the patient is generally taken to a surgical suite and open chest by-pass is performed. Until the by-pass is successfully completed, the area at risk remains starved of blood.

Medical practitioners have attempted to reduce the infarct resulting from the ischemic events suffered during beating heart surgery and angioplasty with drugs and through a technique known as preconditioning. Drugs, for example adenosine and RheothRx, have been tried, and although under some circumstances they may have some effect, they have ultimately proven generally inadequate for one reason or another.

In preconditioning, the cardiac muscle is subjected to short periods of ischemia, for example two or three episodes of 5 minutes of ischemia followed by reperfusion, prior to the angioplasty or other anticipated procedure that will expose the heart to a more prolonged ischemic event. This has been found to reduce the infarct size resulting from the prolonged subsequent ischemia somewhat, but is difficult to perform safely, requires a complex set-up and is an invasive procedure. Importantly, precondition must occur well in advance of the ischemic event. For all these reasons it is generally not a useful procedure, and because it necessarily must occur in advance of the anticipated ischemic event, it is unsuitable for treating ischemia due to heart attacks that have already occurred or are in process.

Under ordinary circumstances, the temperature of the body and particularly that of the blood is maintained by the body's thermoregulatory system at a very constant temperature of about 37° C. (98.6° F.) sometimes referred to as normothermia. The amount of heat generated by the body's metabolism is very precisely balanced by the amount of heat lost to the environment. The circulating blood serves to keep the entire body and particularly the heart, at normothermia. Deep hypothermia (30° C. or lower) has long been known to be neuroprotective, and believed to be cardioprotective as well. More recently, the advantage of mild hypothermia (only as low as 32° C. or even as warm as between 35° C. and normothermia) to ischemic cardiac tissue has been recognized, either before and/or during an anticipated ischemic event such as may occur in beating heart surgery or coronary angioplasty, during an ischemic event such as a heart attack in progress, or soon after an ischemic event such as a heart attack that has already occurred. No satisfactory method of achieving this mild cardiac hypothermia in the human clinical setting, however, has been available before this invention. In rabbits, ice bags or ice-filled surgical gloves have been applied directly to the heart in an open-chest procedure. This method is clearly very invasive, clumsy and lacks control over the level of hypothermia applied. Other attempts have been made using cooling blankets or externally applied ice bags or iced blankets. These methods are slow, lack adequate control over the patient temperature, are not directed to the heart muscle and therefore are not effective in the human clinical setting to adequately reduce cardiac temperature, especially in obese patients.

Another method of achieving cardiac hypothermia has been proposed, that of pericardial lavage using a two-lumen catheter, with the distal ends of both lumens (one input and one outflow) sealed inside the pericardial sack. A cold solution such as cold saline is circulated within the pericardial sack to cool the heart muscle. While this method is rapid and directed to the cardiac muscle, it is highly invasive, requires surgical access to the pericardial sack which generally requires either an open chest procedure or a thoracotomy, involves piercing the pericardial sack, and introducing superfluous fluid into the pericardial sack of a beating heart, all with the attendant risks. If used, it requires the full surgical suite and delicate and highly skilled surgical technique. The surgical invasion of the pericardial sack is generally not acceptable to practitioners.

Thus, although mild cardiac hypothermia provides protection against infarct resulting from a cardiac ischemic event, the existing methods of achieving cardiac hypothermia are inadequate and unacceptable; a better method of achieving mild hypothermia of the heart that is fast, controlled and less invasive is needed.

SUMMARY OF THE INVENTION

The present invention provides a method for inducing controlled hypothermia of the heart, using an intravascular heat exchange device in the nature of a catheter. The intravascular heat exchange device is inserted into the vasculature of a mammalian patient and is thereafter utilized to cool blood that is flowing to the patient's heart. In this manner, hypothermia of the myocardium is achieved. Myocardial hypothermic treatment in accordance with this invention may be useable to prevent or lessen myocardial infarction in patient's who are suffering from acute myocardial ischemia. Also, the myocardial hypothermic treatment in accordance with this invention may be useable to prevent, deter, minimize or treat other types of damage to the myocardium such as toxic myocardial damage that can occur during or after administration of certain cardiotoxic drugs or exposure to cardiotoxic agents. Also, the myocardial hypothermic treatment in accordance with this invention may be useable to prevent, deter, minimize or treat certain cardiac disorders such as cardiac arrhythmias and the like.

The heart is the body's pump to pump blood throughout the body. A normal heart pumps blood at a rate of 3 liters per minute per square meter and the average human is 1.7 square meters, so the average heart pumps about 5.1 liter of blood per minute for entire life of the person. Under normal conditions, the blood is maintained at a very constant temperature of 37° C., and this in turn keeps the heart (and the rest of the body) at a very constant temperature of 37° C. The heart temperature is maintained by both the temperature of the arterial blood and the venous blood, in addition to the small amount of arterial blood that is re-circulated through the coronary arterial tree to feed the heart muscle (estimated to be 4% of the total circulation) the average heart pumps about 306 liters of blood per hour, blood that is all circulated through the heart cavities. Therefore cooling the venous blood that enters the heart will effectively cool the heart by direct contact with the cardiac muscle in the cardiac cavities.

As may be seen, cooling the venous blood in the vena cava also effectively cools the arterial blood that is circulated through the cardiac arteries. After being cooled in the vena cava, the blood first enters the right atrium, is then pumped through the lungs (which expose the blood to air at room temperature which is generally less than normothermia), from whence it is returned to the left atrium, and then to the left ventricle. The left ventricle pumps the oxygenated blood to the body through the aorta, and the first arteries to branch off the aorta are the coronary arteries. Thus the blood will be circulated through the arterial tree of the heart without ever having picked up metabolic heat from the rest of the body. The heart is thus cooled both by direct contact with the cooled blood and by having the cooled blood circulated through the coronary arteries before picking up metabolic heat from the outlying capillary beds.

Described herein is a method for reducing the size of any infarct that results from a cardiac ischemic event by inserting a cooling catheter having a heat exchange region into the vasculature of a patient, placing the heat exchange region into the blood stream flowing to the heart, cooling the blood as it passes the heat exchange region and thus directing cooled blood to the heart muscle before, during and/or after an ischemic event for a sufficient length of time to reduce the temperature of the heart. The method advantageously is practiced by placing the heat exchange region of the catheter into the patient's vena cava, either the inferior vena cava (IVC) or the superior vena cava (SVC), and the heat exchange region may even be placed partially or totally within the heart itself.

The cooling catheter may be introduced into the patient in any acceptable means, for example percutaneously through the femoral vein into the IVC or via the internal jugular vein into the SVC, by surgical cut-down, or by surgical placement in a patient with an open chest.

The cooling of the cardiac muscle is advantageous if performed after a cardiac ischemic event, for example a heart attack, and is advantageous if performed before an anticipated ischemic event, for example before or during coronary angioplasty or beating heart surgery, and if performed during an ischemic event, for example during a heart attack in progress or during an angioplasty or beating heart surgery.

The cooling of the blood may be done by a cooling catheter having various acceptable types of cooling regions, for example a cooling catheter with a balloon for receiving the circulation of heat transfer fluid that is cooled outside of the body of the patient. Of particular value is the efficiency of a multi-lobed heat exchange balloon. Other heat exchange elements, however, are also useful in this method. For example, flexible metallic heat exchange regions or heat exchange regions with multiple heat exchange elements would be acceptable for practicing the patented method.

While the heart may experience some harmful effects of when subjected to very deep hypothermia such as arrhythmia's at temperatures below 30° C., profound reduction of infarct resulting from ischemia may be experienced as a result of mild hypothermia of only a few degrees below normothermia, for example hypothermia as mild as 35° C. or above, thereby enjoying the benefits of hypothermia while avoiding the harmful effects of deep hypothermia. Therefore cooling the heart to mild levels of hypothermia above 32° C. is preferred in this method. These temperature targets, of course, will vary somewhat from patient to patient, and from circumstance to circumstance.

Beside the level of hypothermia, the time during which the hypothermia is administered may vary according to the circumstances. For example, the heart may be cooled for a short period of time and then rewarmed, or may be cooled and maintained in a cooled condition for some period of time. For example, a heart attack victim may have the cardiac muscle cooled for an hour, while the hypothermia may be applied during beating heart surgery for several hours.

The heart may also be selectively cooled. That is, the blood directed to the heart may be cooled immediately before being directed to the heart, for example, when the blood is in the IVC, and the blood directed to the rest of the body after leaving the heart may be warmed, for example by a warming catheter in the descending aorta or warming blankets on the skin of the patient. The method of this invention tends to result in a core body temperature that is several degrees warmer than the cardiac temperature achieved, at least initially, and this difference can be accentuated and prolonged by the use of warming blankets or other means to warm the blood of the patient after the cooled blood has left the heart of the patient.

These and other objects and advantages of the invention can be better understood with reference to the drawings and the detailed description of the embodiments of the invention described below.

BRIEF DESCRIPTION OF THE DRAWINGS

FIG. 1 is a depiction of a heat exchange catheter in the vasculature of a patient with the heat exchange region of the catheter located in the vena cava of the patient.

FIG. 2 is a cross-sectional view of the shaft of a heat exchange catheter.

FIG. 3 shows a side view of the heat exchange region of a heat exchange catheter as assembled.

FIG. 4 shows the shaft member of the heat exchange catheter of FIG. 3.

FIG. 5 shows the balloon configuration of the catheter assembly of FIG. 3.

DETAILED DESCRIPTION

Figure 6:
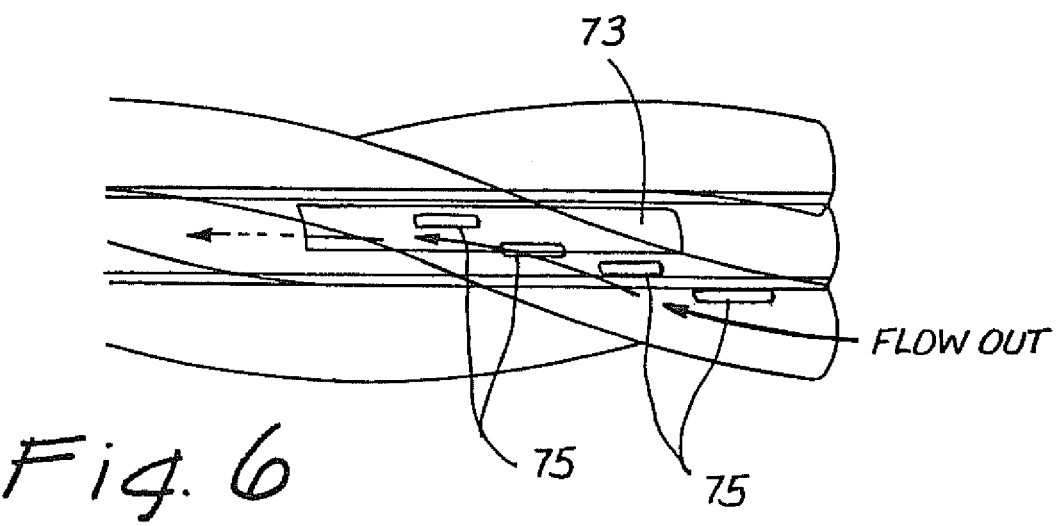
FIG. 6 is a view of a portion of the heat exchange catheter of FIG. 3 illustrating outflow of heat exchange fluid.
Figure 7:
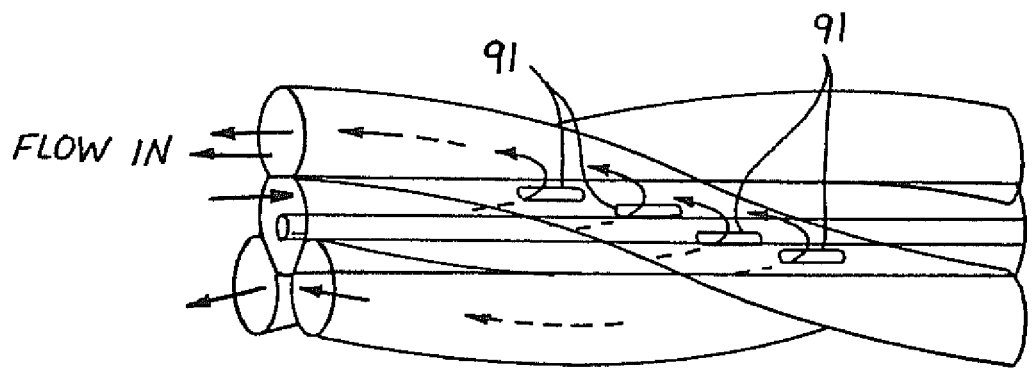
FIG. 7 is a view of a portion of the catheter of FIG. 3 illustrating inflow of exchange fluid.

The present invention comprises a method of cooling the beating heart to protect myocardial tissue from infarct as a result of ischemia. The heart is cooled by placing a heat exchange catheter having a heat exchange region in contact with blood flowing to the heart, for example, blood in the IVC, cooling the heat exchange region to a temperature lower than that of the blood, for example circulating saline at 2° C. through the heat exchange region to cool the heat exchange region to about 2° C. thereby cooling the blood to a temperature below normothermia, and maintaining the cooling for a long enough time to reduce the temperature of the heart.

In intravenous cooling such as that described in the previous paragraph, a heat exchange region is placed in the bloodstream and maintained at a lower temperature than the blood. The rate of cooling blood by means of a heat exchange region in contact with flowing blood depends on a number of factors. One is the difference in temperature between the blood and the heat exchange region in contact with that blood. Other factors include the specific heat of the blood, the amount of surface area of the heat exchange region in contact with the blood, and the heat transfer coefficient between the blood and the surface of the heat exchange region. Certain other factors may also effect the efficiency of heat transfer between the heat exchange region and the colloidal fluid that is blood, such as turbulent flow (see e.g. U.S. Pat. No. 5,624,392 to Saab, col. 11, ll. 56-60) to enhance heat exchange. Where the heat exchange region is cooled by the circulation of heat exchange fluid, counter-current flow between the blood and the heat exchange fluid is important so that the heat exchange fluid flows through the heat exchange region in a direction opposite that of the blood flow. In this way, the warm blood flows over the warmest part of the heat exchange region first toward the coldest part of the heat exchange region. It has been found that a balloon heat transfer catheter of the type described below with the heat exchange region placed in contact with blood flowing in the IVC is a satisfactory method of practicing this invention, although other heat exchange catheters with other types of heat exchange regions are within the scope of the invention.

Essentially all the blood flow into the heart cavities flows through the vena cava, the IVC below the heart and the SVC above the heart. It is estimated that in the ordinary human ⅔ of the total venous return to the heart flows through the IVC and ⅓ through the SVC. The vena cava is a large vessel; in the human patient, the IVC is generally about 200 millimeters long and generally ranges between about 160 millimeters and 260 millimeters. In diameter it varies somewhat over that length, but averages about 21 millimeters in diameter. Cooling blood flowing through the vena cava provides an effective way of inducing mild hypothermia to the heart. Blood flowing through the vena cava is flowing directly to the heart cavities. It cools the heart directly by contact with the heart muscle. The blood that feeds the cardiac arteries would also generally be relatively cool since blood cooled in the vena cava travels only to the lungs before being pumped through the cardiac arteries. In the lungs the blood is exposed to air at ambient temperature which is usually below normothermia, and the blood does not travel through the rest of the body where it would pick up metabolic heat.

Because large volumes of blood are cooled by the method of the invention, the temperature of the entire body may be somewhat depressed, that is the patient may experience what is sometimes called whole body hypothermia. Although it is generally the case the body functions most efficiently at normothermia, some whole body hypothermia is acceptable and in some situations may even by therapeutic. In any event, as the example detailed below describes, the temperature of the body core other than the cardiac muscle tends to lag the hypothermia experienced by the cardiac muscle, and this results in even shallower hypothermia than that experienced by the cardiac muscle. It is often the case that the application of cooling to the heart with the heat exchange region of the cooling catheter in the vena cava tends to be fairly short, perhaps an hour or less, so the core cooling experienced by the whole body while practicing this method is generally not harmful.

FIG. 1 shows a heat exchange catheter 10 having a heat exchange region 12 located in the IVC 14 of a patient. The heat exchange region is maintained at a temperature below that of the blood, perhaps as cold as 0° C., so that blood flowing past the heat exchange region gives off heat to the heat exchange region and thus is cooled. The cooled blood, indicated by arrows in FIG. 1, flows into the heart 16 and cools the heart.

The balloon heat exchange catheter may be placed in the vasculature of a patient by for example, percutaneously inserting it using the well known Seldinger technique into the femoral vein 18 and advancing it toward the heart until the heat exchange region 12 is located the vena cava of the patient. In one preferred method, a balloon heat exchange catheter has a heat exchange region comprising a balloon with mechanisms for circulating cold saline through the balloon as the heat exchange fluid. The balloon is percutaneously placed into the femoral vein and advanced to locate the heat exchange balloon in the IVC. As shown in FIG. 2, the shaft 18 of the heat exchange catheter has three lumens therein, an inflow lumen 20 for the flow of heat exchange fluid to the heat exchange region, an outflow lumen 22 for the flow of heat exchange fluid from the heat exchange region, and a working lumen 24 that may be used for a guide wire or the administration of medicaments from the proximal end of the catheter through the distal end of the catheter.

The inflow lumen is in fluid communication with the distal end of the balloon; the outflow lumen is in fluid communication with the proximal end of the balloon. The heat exchange fluid is circulated from outside the body, down the inflow lumen to the distal end of the balloon, through the balloon, and back out the outflow lumen. In this example this results in the heat exchange fluid flowing in the opposite direction of the blood, i.e. counter-current flow. This counter-current heat exchange between flowing liquids is the more efficient means of exchanging heat.

By controlling the temperature of the saline, the temperature of the balloon may be controlled. The saline may be cooled outside the body by, for instance, an external heat exchanger 26, to cool the saline to as low as 0° C. The balloon is thereby cooled to as low as 0° C., at least at the point where the heat exchange fluid first begins to exchange heat with the blood. As will be readily appreciated, a temperature gradient is established along the length of the balloon. Where the heat exchange fluid first enters the balloon, the balloon is at its coldest. If the heat exchange fluid is at 7° C. for example, when it exits the central lumen and enters the balloon, the surface of the balloon will be essentially 7° C. At that point if the blood is at normothermic, that is 37° C., the DT would be 30° C. and the blood would give off heat through the balloon to the heat exchange fluid. It should be noted that not all the heat exchanged between the blood and the heat exchange fluid will be at the heat exchange region. Some heat may be exchanged between the blood flowing in the femoral vein and the vena cava so the temperature at the coldest point on the heat exchange region may be as warm as 7° C. even if the saline is cooled by the external cooler to as cold as 0° C. It is preferable to exchange the maximum amount of heat in the IVC near the heart by means of the heat exchange region, but the blood in the femoral vein and IVC which may exchange heat with the shaft of the catheter ultimately flow past the heat exchange region and into the heart, so that heat exchanged by this portion of the heat exchange catheter also serves somewhat to cool the heart. Therefore, in evaluating the performance of the catheters used in the preferred embodiments of this invention, the temperature at the inlet to the heat exchange catheter, that is soon after it leaves the external heat exchanger, and the temperature at the outlet of the heat exchange catheter, that is just before it enters the external heat exchanger, in conjunction with the flow rate of heat exchange fluid in the catheter, can give a useful estimate of the heat exchanged with the blood directed to the heart, although it would include both the heat exchanged at the heat exchange region and heat exchanged along the shaft. For example, in the multi-lobed heat exchange catheter described in detail below, the temperature at the inlet may be measured at about 4° C. and the temperature at the outlet at about 11° C. The flow rate in the catheter may be about 450 ml/min. This indicated a total heat exchange of about 220 watts of energy, a performance adequate for practicing the method of this invention.

It should be noted that the exchange of heat from the body may be controlled by controlling the external heat exchanger. For example, if maximum temperature reduction were desired, maximum power to the heat exchange region would result in the coldest possible heat exchange fluid and thus the largest DT between the heat exchange fluid and the blood. Once the target temperature had been reached and the number of watts needed to be removed from the blood to maintain the target temperature was less, the watts transferred from the body could be reduced by reducing the power to the external heat exchanger. This would in turn increase the temperature of the heat exchange fluid as it left the external heat exchanger and entered the catheter, which would decrease the DT between the blood and the heat exchange fluid, and thus reduce the watts removed from the bloodstream.

The external heat exchanger may be, for example, a hot/cold plate formed of a number of thermoelectric units such as Peltier units, or other hot or cold elements in contact with a thermal exchange bag through which the heat exchange fluid is circulated. If the bag is sealed and forms a closed circuit with the heat exchange fluid in the catheter, the heat exchange fluid may be heated or cooled exterior of the body without ever being exposed to the air. If the saline is initially sterile, it may thereby be maintained sterile, an advantage for fluid that is circulated through the body. Although the heat exchange fluid is not intentionally in contact with the blood, if a leak should occur it would be a significant advantage to use sterile heat exchange fluid.

The external heat exchange unit, in turn, may controlled by controller 28 that may be pre-programmed or may be reactive to a temperature sensor 30 that senses the temperature of the patient. As will be readily appreciated by those of skill in the art, the temperature sensor may sense the temperature of the heart itself to the patient's body temperature as measured by a rectal sensor, an esophageal sensor, a tympanic sensor or the like. It has been found that the temperature sensors in the heart tissue when a heat exchange balloon is located in the vena cava tends to more closely reflect the temperature of the heat exchange balloon than do the rectal, esophageal or tympanic sensors, but that these various sensors correlate well with each other, and thus, with the appropriate compensation factors, any one of them may be used to control the temperature of the heat exchange region for purposes of inducing and controlling cardiac hypothermia.

If the external heat exchanger is able to both heat and cool, as is the case for example in the Peltier elements described above, the heat exchange fluid may be heated or cooled in response to the signal from the sensor. If the external heat exchange unit is able to be controlled as to the amount of heating or cooling it provides, the degree of heating or cooling supplied by the heat exchange unit may be controlled in response to the signal received from the sensor. As will be seen in the example described below, this will allow the operator to cool the heart to a predetermined temperature, maintain the heart at a predetermined temperature for a length of time, and add heat to the blood to warm the heart at a chosen point. In practice, the controller receives a signal that represents the temperature of the heart tissue. As this temperature nears the target temperature, the controller causes the external heat exchanger to reduce the amount of cooling applied to the heat exchanger. By internal calculations, the rate of decrease of the temperature of the heart tissue is calculated relative to the amount of energy applied by the external heat exchanger, and as the heart tissue nears and finally reaches the target temperature, the precise amount of cooling that must be applied by the external heat exchanger to cause a rate of change of essentially 0 is known. By application of this amount of cooling by the external heat exchanger when the heart reaches the target temperature, the heart is essentially maintained at precisely this temperature. In this way, by use of the controller receiving a signal from the patient's body that represents heart temperature, the operator is able to precisely control the level of hypothermia applied. By determining how long the controller will maintain this level of hypothermia and when it will begin to re-heat, the length of the hypothermia applied to the heart may also be precisely controlled.

Although the heat exchange region shown in FIG. 1 is a simple, single lobed balloon, the heat exchange region may be of various advantageous configurations. One effective catheter for exchanging heat with the blood in the vena cava is a heat exchange balloon catheter having a heat exchange region that is a multi-lobed balloon and has the temperature of the heat exchange region controlled by controlling the temperature of heat exchange fluid circulated through the balloon.

Such a catheter is depicted in FIG. 3 through FIG. 12. The assembled catheter 31 (FIG. 3) has a four-lumen, thin-walled balloon 33 (FIG. 5) which is attached over an inner shaft 35 (FIG. 4).

Figure 9:
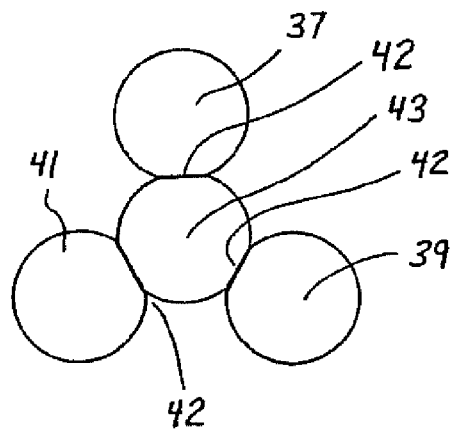
FIG. 9 is a cross-sectional view of the balloon of FIG. 5 taken along the line 9-9.
Figure 10:
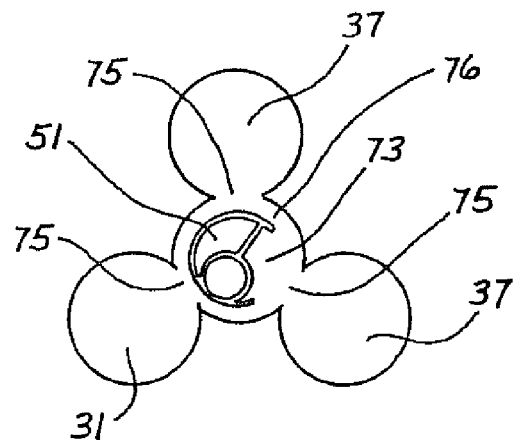
FIG. 10 is a cross-sectional view of the catheter of FIG. 3 taken along the line 10-10.
Figure 11:
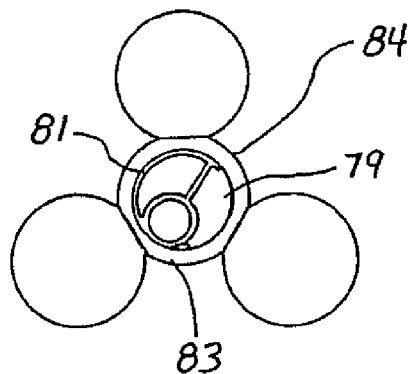
FIG. 11 is a cross-sectional view of the catheter of FIG. 3 taken along the line 11-11.
Figure 12:
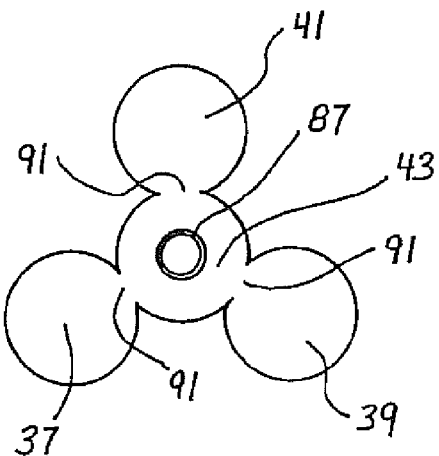
FIG. 12 is a cross-sectional view of the catheter of FIG. 3 taken along the line 12-12.

The cross-sectional view of the four-lumen balloon is shown in FIG. 9. The balloon has three outer lumens 37, 39, 41 which are wound around an inner lumen 43 in a helical pattern. All four lumens are thin walled balloons and each outer lumen shares a common thin wall segment 42 with the inner lumen 43. The balloon is approximately twenty-five centimeters long, and when installed, both the proximal end 67 and the distal end 89 are sealed around the shaft in a fluid tight seal.

Figure 8:
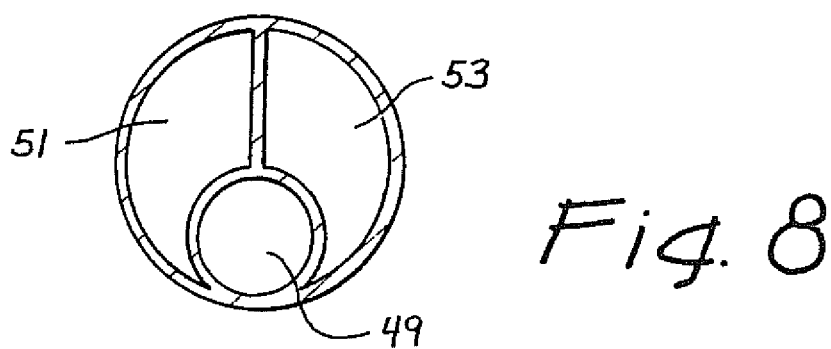
FIG. 8 is a cross-sectional view of the shaft of FIG. 3 and FIG. 4 taken along the line 8-8.

The shaft 35 is attached to a hub 47 at its proximal end. The cross section of the proximal shaft is shown at FIG. 8. The interior of the shaft is configured with three lumens, a guide wire lumen 49, an inflow lumen 51 and an outflow lumen 53. (For purposes of this description the inflow lumen is lumen 51, and the outflow lumen is 53. As one of skill in the art may readily appreciate, the inflow and outflow lumens may be reversed if desired.) At the hub, the guide wire lumen 49 communicates with a guide wire port 59, the inflow lumen is in fluid communication with an inflow port 55, and the outflow lumen is in communication with an outflow port 57. Attached at the hub and surrounding the proximal shaft is a length of strain relief tubing 61 which may be, for example, heat shrink tubing.

Between the strain relief tubing and the proximal end of the balloon, the shaft 35 is extruded with an outer diameter of about 0.118 inches. The internal configuration is as shown in cross-section in FIG. 8. Immediately proximal of the balloon attachment 67, the shaft is necked down 63. The outer diameter of the shaft is reduced to about 0.100 to 0.110 inches, but the internal configuration with the three lumens is maintained. Compare, for example, the shaft cross-section of FIG. 8 with the cross-section of the shaft shown in FIG. 10 and FIG. 11. This length of reduced diameter shaft remains at approximately constant diameter of about 0.10 to 0.11 inches between the necked down location at 63 and the necked down location at 77.

At the necked down location 63, a proximal balloon marker band 65 is attached around the shaft. The marker band is a radiopaque material such as a platinum or gold band or radiopaque paint, and is useful for locating the proximal end of the balloon by means of fluoroscopy while the catheter is within the body of the patient.

At the marker band, all four lobes of the balloon are reduced down and fastened to the inner member 67. This may be accomplished by folding the balloon down around the shaft, placing a sleeve, for example a short length of tubing, over the balloon and inserting adhesive, for example by wicking the adhesive, around the entire inner circumference of the sleeve. This simultaneously fastens the balloon down around the shaft and creates a fluid tight seal at the proximal end of the balloon.

Distal of this seal, under the balloon, an elongated window 73 is cut through the wall of the outflow lumen in the shaft. Along the proximal portion of the balloon, five slits, e.g. 75, are cut into the common wall between each of the outer balloon lumens and the inner lumen 43. (See FIG. 10 and FIG. 6.) Because the outer lumens are twined about the inner lumen in a helical fashion, each of the outer tubes passes over the outflow lumen of the inner shaft member at a slightly different location along the length of the inner shaft, and therefore an elongated window 73 is cut into the outflow lumen of the shaft so that each outer lumen has a cut 75 where that lumen passes over the window in the shaft. Additionally, there is sufficient clearance between the outer surface of the shaft and the walls of the inner lumen 43 to create sufficient space to allow relatively unrestricted flow through the 5 slits 75 in each outer lumen 37,39,40 to the outflow lumen of the shaft 53.

Distal of the elongated window in the outflow lumen, the inner member 43 of the four-lumen balloon is sealed around the shaft in a fluid tight seal 82. The outflow lumen is plugged 79, and the wall to the inflow lumen is removed. (See FIG. 11.) This may be accomplished by necking down the shaft 77 to seal the outflow lumen shut 79, removing the wall of the inflow lumen 81, piercing a small hole in the wall of the inner lumen 84 and wicking UV curable adhesive into the hole and around the entire outside of the shaft, and curing the adhesive to create a plug to affix the wall of the inner lumen of the balloon around the entire outside of the shaft 83. The adhesive will also act as a plug to prevent the portion of the inner lumen proximal of the plug from being in fluid communication with the inner member distal of the plug.

Just distal of the necked down location 77, the guide wire lumen of the shaft may be terminated and joined to a guide wire tube 87. The guide tube then continues to the distal end of the catheter. The inflow lumen 81 is open into the inner lumen of the four-lobed balloon and thus in fluid communication with that lumen.

The distal end of the balloon 89 including all four lumens of the balloon is sealed down around the guide wire tube in a manner similar to the manner the balloon is sealed at the proximal end around the shaft. This seals all four lumens of the balloon in a fluid tight seal. Just proximal of the seal, four slits slits 91 are cut each the common wall between each of the three outer lumens 37, 39, 41 of the balloon and the inner lumen 43 so that each of the outer lumens is in fluid communication with the inner lumen. (See FIG. 5 and FIG. 12.)

Just distal of the balloon, near the distal seal, a distal marker band 93 is placed around the inner shaft. A flexible length of tube 95 may be joined onto the distal end of the guide wire tube to provide a flexible tip to the catheter. Alternatively, a soft tip 98 may be attached over the very distal end of the catheter. The distal end of the flexible tube 97 is open so that a guide wire may exit the tip, or medicine or radiographic fluid may be injected distal of the catheter through the guide wire lumen.

In use, the catheter is inserted into the body of a patient so that the balloon is within a blood vessel. Heat exchange fluid is circulated into the inflow port 55, travels down the inflow lumen 51 and into the inner lumen 43 at the end of the inflow lumen 81. The heat exchange fluid travels to the distal end of the inner lumen and through the slits 91 between the inner lumen 43 and the outer lumens 37, 39, 41.

The heat exchange fluid then travels back through the three outer lumens of the balloon to the proximal end of the balloon. The outer lumens are wound in a helical pattern around the inner lumen. At some point along the proximal portion of the shaft, each outer lumen is located over the portion of the shaft having a window to the outflow lumen 76, 74, 73, and the outer balloon lumens have slits 75, 78, 80 that are aligned with the windows. The heat transfer fluid passes through the slits 75, 78, 80 through the windows 73, 74, 76 and into the out flow lumen 53. From there it is circulated out of the catheter through the outflow port 57. At a fluid pressure of 41 pounds per square inch, flow of as much as 500 milliliters per minute may be achieved with this design.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral vein into the ascending vena cava, it is desirable to have the heat exchange fluid in the outer balloon lumens flowing in the direction from the distal end toward the proximal end of the catheter. This is the arrangement described above. It is to be readily appreciated, however, that if the balloon were placed so that the blood was flowing along the catheter in the direction from distal to proximal, for example if the catheter was placed into the IVC from a jugular insertion, as is illustrated in FIG. 8, it would be desirable to have the heat exchange fluid circulate in the outer balloon lumens from the proximal end to the distal end. Although in the construction shown this is not optimal and would result is somewhat less effective circulation, this could be accomplished by reversing which port is used for inflow direction and which for outflow.

Figure 13:
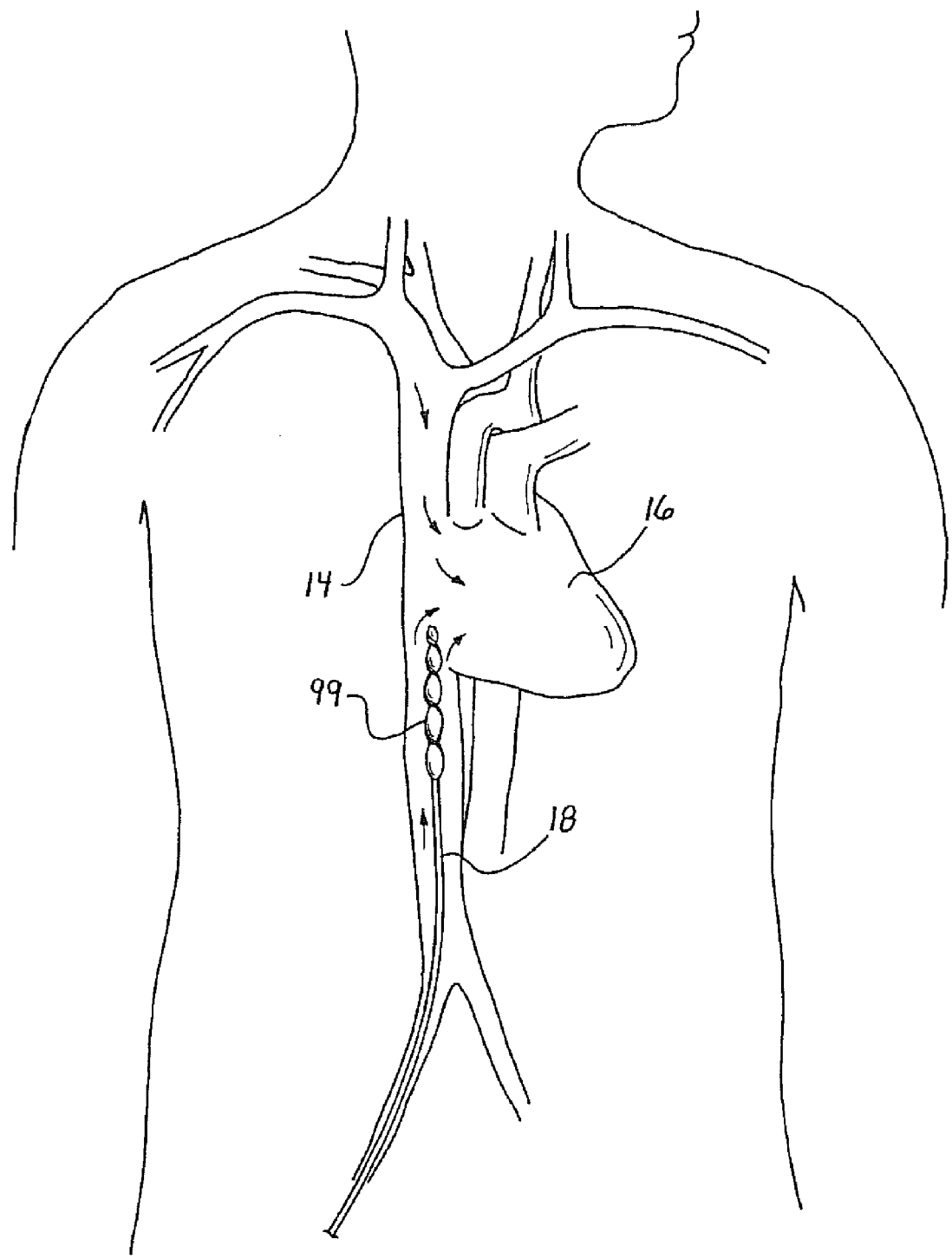
FIG. 13 is an illustration of a heat exchange balloon having a spiral shaped heat exchange region in place in the IVC.
Figure 14:
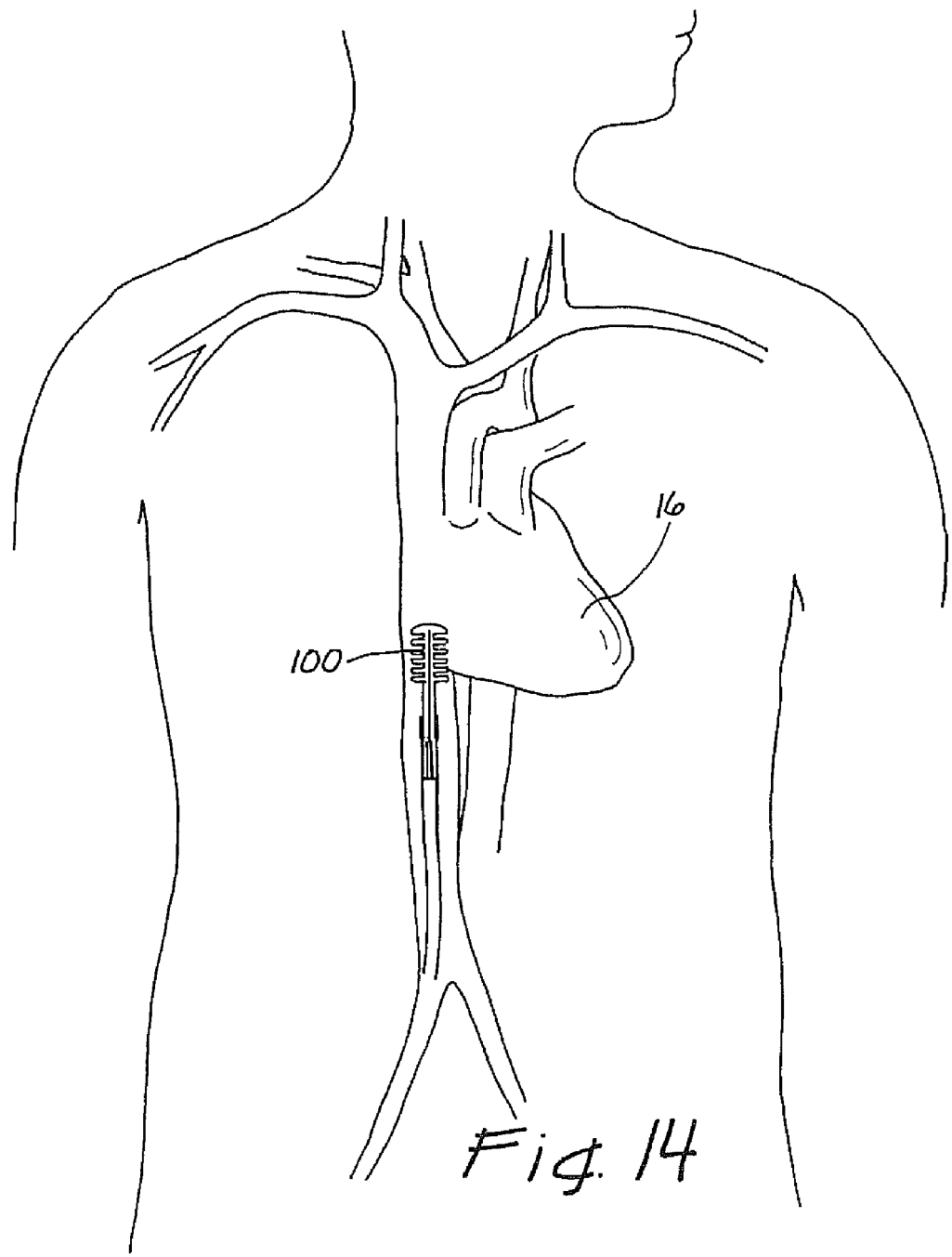
FIG. 14 is an illustration of a bellows shaped heat exchange region in place in the IVC.
Figure 15:
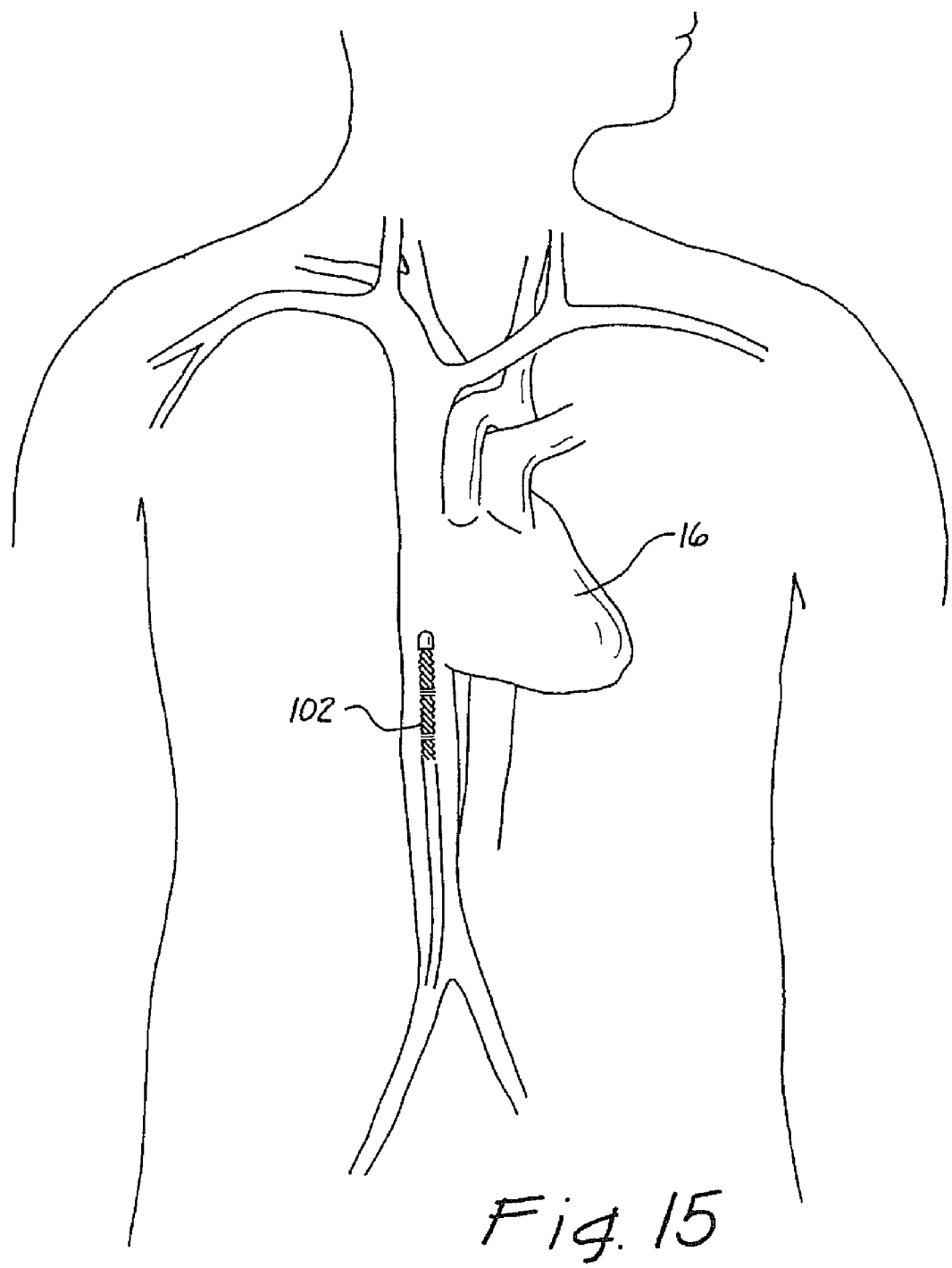
FIG. 15 is an illustration of a flexible metal heat transfer region with spiral shaped heat transfer fins and radial heat transfer fins on the surface of the heat exchange region, said heat exchange region in place in the IVC.
Figure 16:
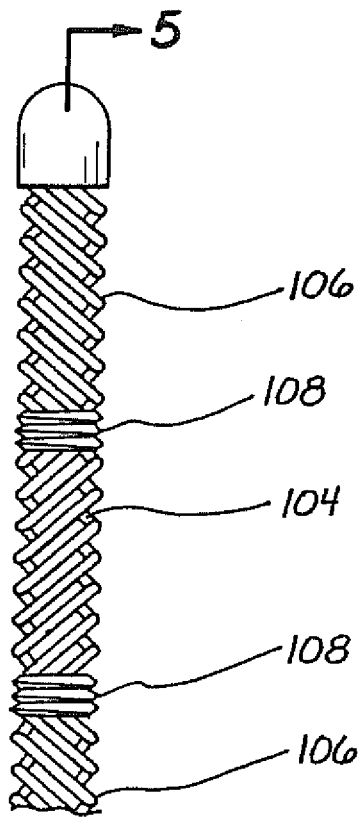
FIG. 16 is an enlarged side view of the heat transfer region of the catheter of FIG. 15.
Figure 17:
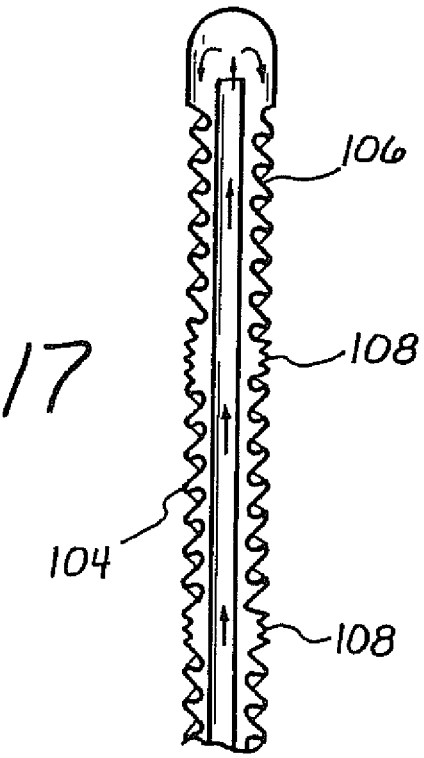
FIG. 17 is a cross-sectional view of the heat transfer region of FIG. 15.
Figure 18:
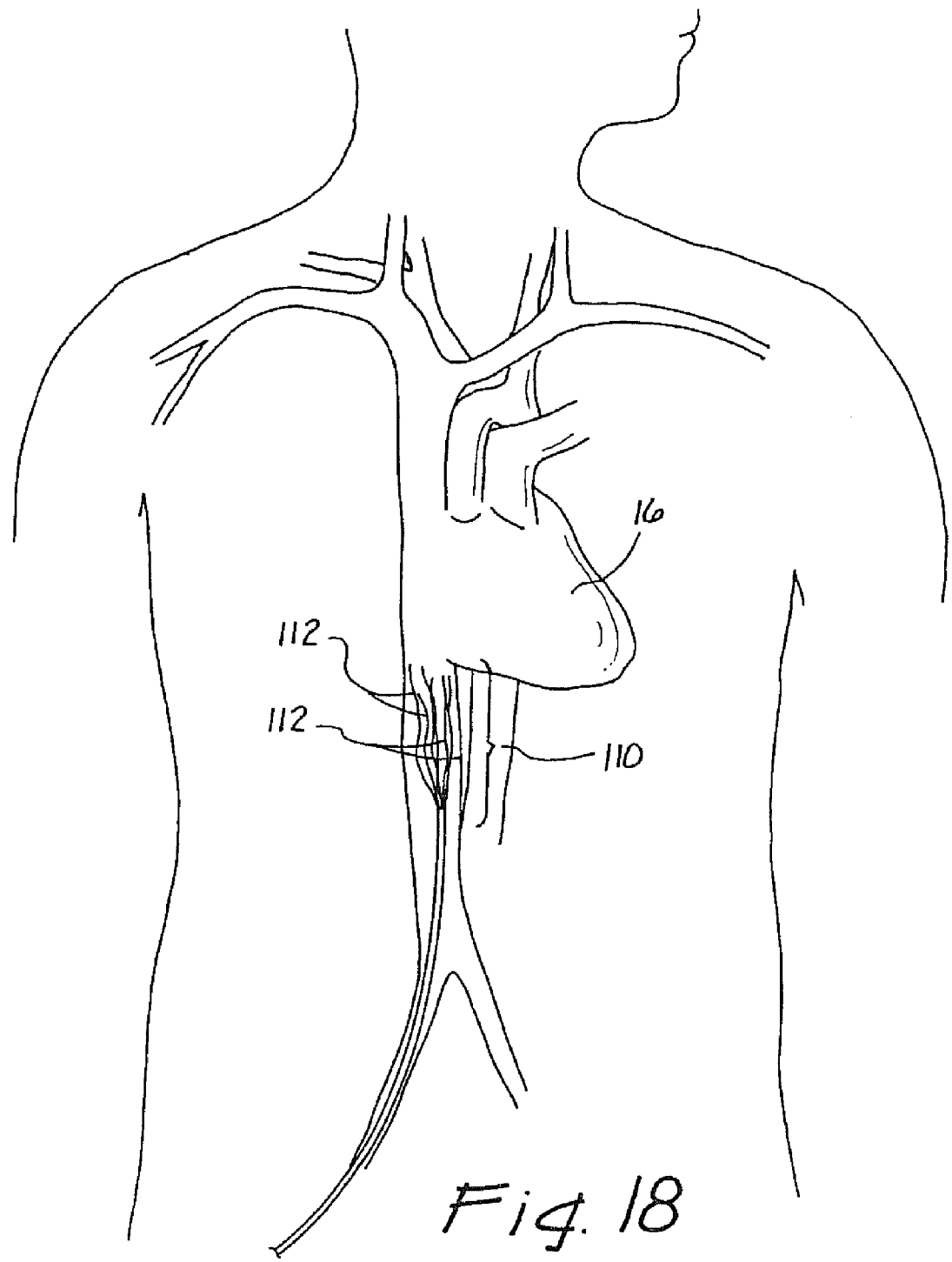
FIG. 18. is an illustration of a heat exchange catheter having a heat exchange region comprising multiple heat exchange elements in place in the vena cava.
Figure 19:
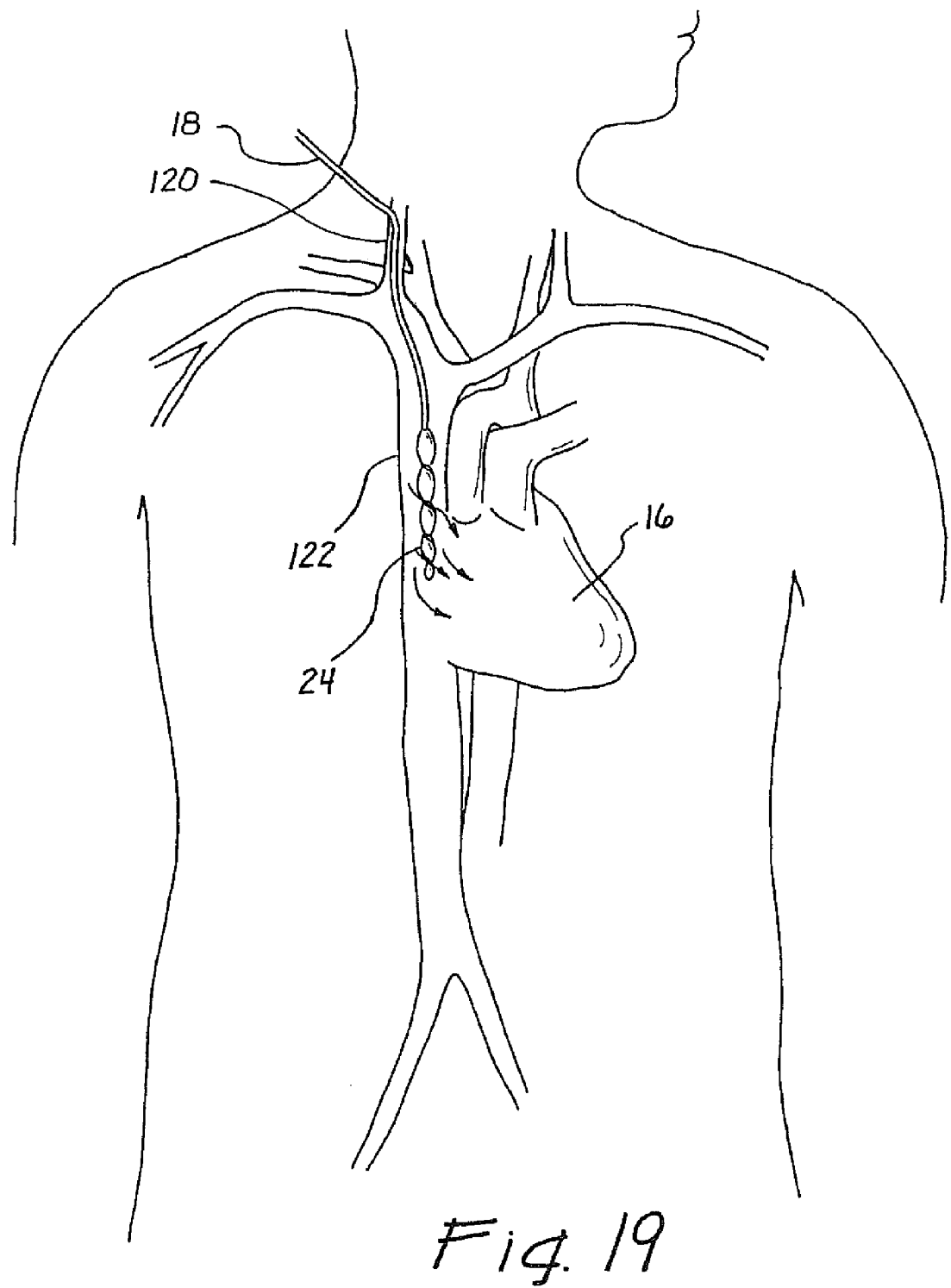
FIG. 19 is an illustration of a heat exchange catheter inserted into a patient via an internal jugular vein insertion, with the heat exchange region in place in the SVC.

As depicted in FIG. 13, a catheter such as that described above, with the heat exchange region 99 located in the IVC provides an advantageous apparatus for the practice of the method of this invention. Other advantageous configurations for the heat exchange region may be employed, however. For example, the heat exchange region may have a bellows-shaped surface 100 as shown in FIG. 6, or the heat exchange region 102 may have a surface shaped with alternating right handed spirals 104 and left handed spirals 106 with a bellows shaped surface 108 between the spirals as shown in FIGS. 14-17. Another acceptable variation of the heat exchange catheter would have a heat exchange region 110 comprising multiple heat exchange elements 112 as illustrated in FIG. 18.

Those of skill in the art will also readily appreciate that, beside the use of different heat exchange regions, other acceptable placements of the heat exchange region may be employed to practice the method of this invention. For example, An internal jugular insertion may be made wherein the catheter is inserted into the internal jugular vein 120 and the heat exchange region advanced to, for example, the SVC 122 as illustrated in FIG. 8. With an internal jugular insertion, if the heat exchange region is only advanced into the SVC, the blood flow will be from the proximal to the distal end of the heat exchange region, i.e. in the same relative direction as with a femoral insertion and placement of the heat exchange region in the IVC, so counter-current flow between the heat exchange fluid and the blood will be maintained with the same catheter as described above.

EXAMPLE

The method of the invention may be described by reference to the following example. In the instance described here, the cardiac cooling method of the invention was performed using 60 B 80 kg. pigs. The study was conducted in accordance with The Guide for Care and Use of Laboratory Animals. Each pig was anesthetized with isoflourane anesthesia, and vascular sheaths were inserted percutaneoulsy in to the femoral artery and vein respectively. A median sternotomy was done, followed by the isolation of the left anterior descending coronary artery. A three lobed heat exchange catheter as described above was inserted into the sheath in the femoral vein and the catheter was advanced until the heat exchange region was in the IVC just below the heart. Saline was circulated through the heat exchange region of the catheter and an exterior heat exchanger. The exterior heat exchanger was in the form of a hot/cold plates formed by a number of Peltier units, and a bag of saline in contact with the plates. The circuit of the saline through the bag and through the catheter including the heat exchange region was closed, and the saline was sterile. The temperature of the Peltier plates, and thus of the saline, was controlled by a lap-top computer using a commercially available control program readily available to and understood by those of skill in the art, and was controlled in response to core temperature sensed by an esophageal temperature sensor of the type typically used in the medical arts.

The core temperature was initially maintained at 38° C. (normothermia for pigs) by adding or removing heat as necessary with the heat exchange catheter. Because the chest had been opened by the sternotomy, this generally comprised adding a small amount of heat to the blood. The left anterior descending coronary artery was occluded for a total of 60 minutes about 213 of the way down its length using a snare. The snare was formed using a suture placed around the descending coronary artery, with both legs of the suture contained within a plastic tube. The snare was tightened and the occlusion formed by sliding the tube down against the artery.

Twenty minutes into the occlusion, the external heat exchanger was turned on with the controller was set to remove heat via the heat exchange catheter to lower the cardiac temperature of the pig at the maximum rate. Heat was removed from the blood flowing through the IVC at a rate that varied somewhat between test animals from about 140 watts to 220 watts, but was generally about 190 watts.

At the end of the 60-minute period of ischemia, the snare was loosened by removing the plastic tube by sliding it away from the artery and off the suture. The removal of the snare restored flow to (re-perfused) the ischemic area. The suture was left, lose but in place around the artery. Cooling in order to maintain the target temperature of 34° C. was maintained for 15 minutes after the removal of the occlusion. In the pigs receiving hypothermia, there was thus a total of 55 minutes of cooling: beginning after 20 minutes of occlusion; 40 minutes of cooling during occlusion; then 15 more minutes of cooling after re-perfusion.

After the period of cooling (55 minutes) the external heat exchanger was switched to begin heating, and the temperature of the saline circulating through the heat exchange catheter was raised to 41° C. This in turn began warming the blood and rewarming the pig toward normothermia.

The control pigs were maintained at normothermia (38° C.) initially and during occlusion, and this temperature was maintained for an additional three hours after reperfusion. In the hypothermic pigs, re-warming toward 38° C. was allowed to occur for 2 hours and 45 minutes, that is also until three hours after reperfusion. At the end of this period (4 hours after the initial occlusion), the suture was again tied off around the artery to occlude the vessel, and monastral blue dye was injected into the left ventricular cavity to define the ischemic area at risk. The dye stained all the areas of the heart that were vascularized, and since the suture was tied off around the cardiac artery at the same location as originally occluded, the area at risk would be unstained and would visually accurately define the area at risk during the original ischemia.

The heart was harvested to analyze the effect of the hypothermia on infarct resulting from the ischemic event. The heart was excised, sliced into 0.5 to 1.0 cm slices, and the slices were immersed into 1% triphenyltetrazolium chloride (TTC) for 15 minutes to stain the viable tissue. Nonviable tissue is not stained by TTC. The myocardial slices were photographed using a digital camera and the area at risk, and the infarction zones were quantified using image analysis software. Six animals were studied with hypothermia, while an additional six animals served as controls. For the controls, the heat exchange catheter was placed into the IVC and the controller set to maintain the esophageal temperature 38° C. Otherwise, the procedure was identical for the experimental hypothermia animals and the controls. Results below are expressed as 1) Area at risk (AAR), and 2) Percent of AAR that suffered infarct.

Results:

| | HYPOTHERMIC | | | CONTROL | |
|---|---|---|---|---|---|
| Pig # | AAR (% LV) | IF/AAR (% AAR) | Pig # | AAR (% LV) | IF/AAR (% AAR) |
| 1 | 11.3 | 0.0 | 1 | 25.4 | 49.1 |
| 2 | 13.6 | 0.0 | 2 | 12.6 | 35.9 |
| 3 | 11.2 | 0.0 | 3 | 14.9 | 44.8 |
| 4 | 21.1 | 0.8 | 4 | 33.6 | 45.1 |
| 5 | 18.2 | 0.0 | 5 | 17.7 | 61.5 |
| 6 | 23.7 | 12.8 | 6 | 10.4 | 47.0 |
| Mean ± SD | 16.6 ± 5.3 | 2.3 ± 5.3 | Mean ± SD | 19.1 ± 8.8 | 47.2 ± 8.3 |
| P Value Hypothermic vs. Normothermic | P = NS | P < 0.000005 | | | |

Figure 20:
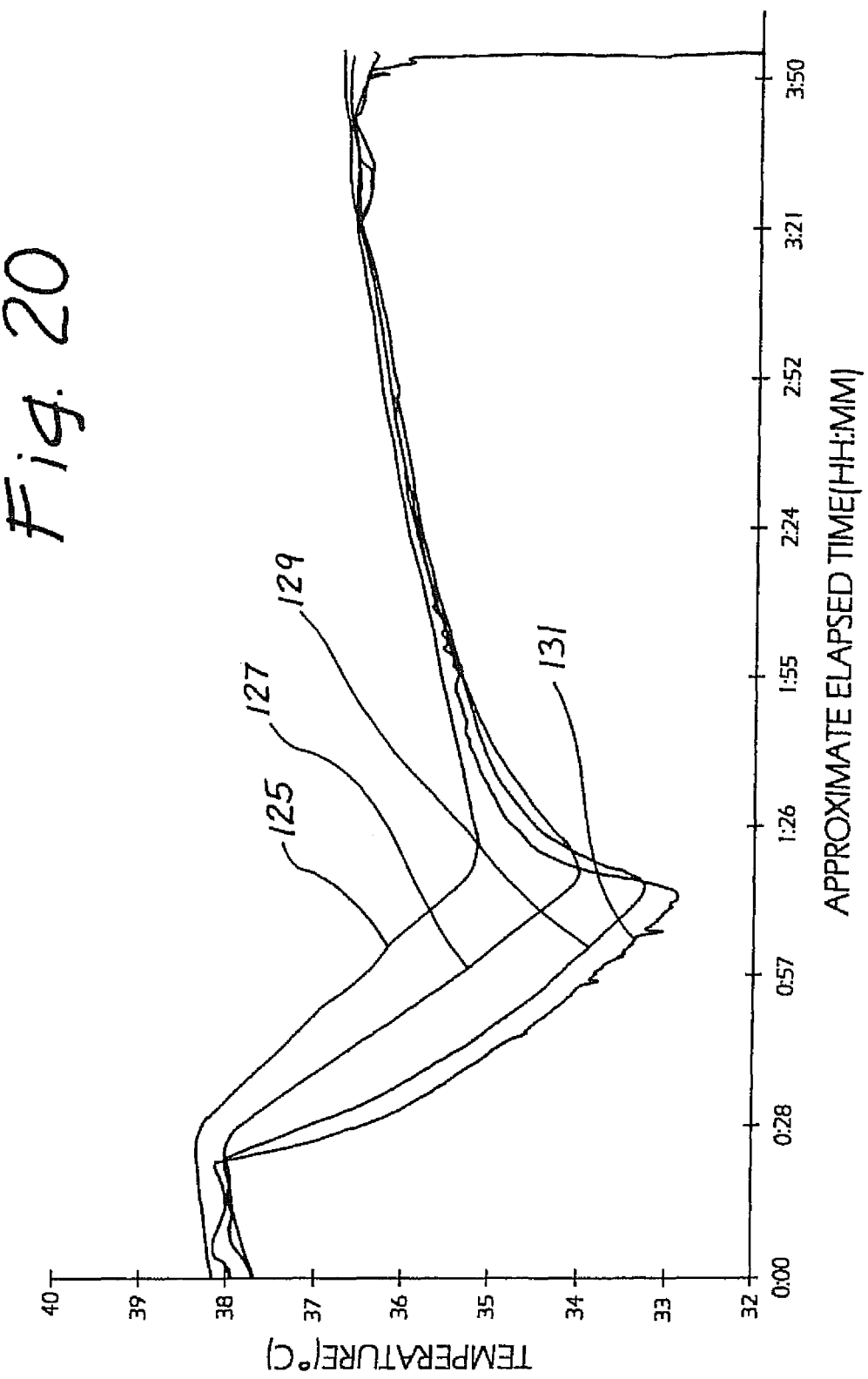
FIG. 20 is a graph of the body temperature during cooling as measured at different locations in the body.

It should be noted that the core temperature of the pig as measured by the tympanic or rectal probe never reached as low a temperature as did the heart itself. A graph showing the temperatures as measured at different locations during one experiment is depicted in FIG. 20. The cardiac temperature was measured by temperature sensors located in the muscle of the left ventricle and of the left atrium. Temperatures were also measured by sensors in the rectum, in the eardrum (tympanic) and in the esophagus. All of the temperatures measured away from the heart itself tended to lag the cardiac temperature, sometimes as much as 2° C. Presumably the fact that the heart was contacted with the cool blood first, and even warmed that blood somewhat before it went out to other locations would explain this difference.

If the heart had reached a target temperature, and the rate of cooling had been reduced to only that necessary to maintain that target temperature, the rate at which the rest of the body would have approached equilibrium would have slowed considerably, and the core body temperature as measured away from the heart would have continued to lag. Presumably, however the body would ultimately reach equilibrium at some hypothermic temperature.

This, however, would take a long time, and in the time while the heat exchange catheter was cooling the heart at hypothermic temperature, the body temperatures never reached equilibrium. Once the heat exchange catheter began to warm the blood, the entire body began to experience warming, and therefore the body core away from the heart never experienced hypothermia as deep as that experienced by the heart. For the times involved in the hypothermic treatment of the method, and for the depth of hypothermia involved, the whole body cooling that resulted was within acceptable limits.

In humans, the same method of applying hypothermia can be used to reduce infarct resulting from an ischemic event. A multi-lobed balloon catheter such as that described above, may be percutaneously placed through the femoral vein so that the heat exchange region is located in the IVC or through the internal jugular vein so that the heat exchange region is located in the SVC, and the blood therein cooled by cooling the heat exchange region (the balloon) by circulating cold saline through the cooling catheter. Saline at about 0° C. can be circulated without undue damage to the blood. A controller receiving a signal representing cardiac temperature, either directly or through some surrogate such as esophageal or tympanic temperature, can control the heat exchange catheter to achieve a target temperature and maintain that temperature. As was the case with the pigs, the heat removed from the blood also results in overall temperature reduction in the whole body since the body is unable to generate sufficient heat to replace that amount removed by the heat exchange catheter, but the heart tends to cool more rapidly than that of the rest of the body. The whole body cooling may be desirable in some instances for therapeutic reasons, for example for neuroprotection is some global ischemia is experienced, but at least at the mild levels of hypothermia in the method of the invention, and for the time lengths expected, therapeutic hypothermia of the heart is obtained by this technique without undue injury to the patient. It is anticipated that means to inhibit shivering using drugs such as meperidine, Thorazine, Demerol, phenegran or combinations thereof, or applying heat to the skin surface may be necessary to prevent or reduce shivering in unanesthesized patients receiving hypothermic therapy.

Figure 21:
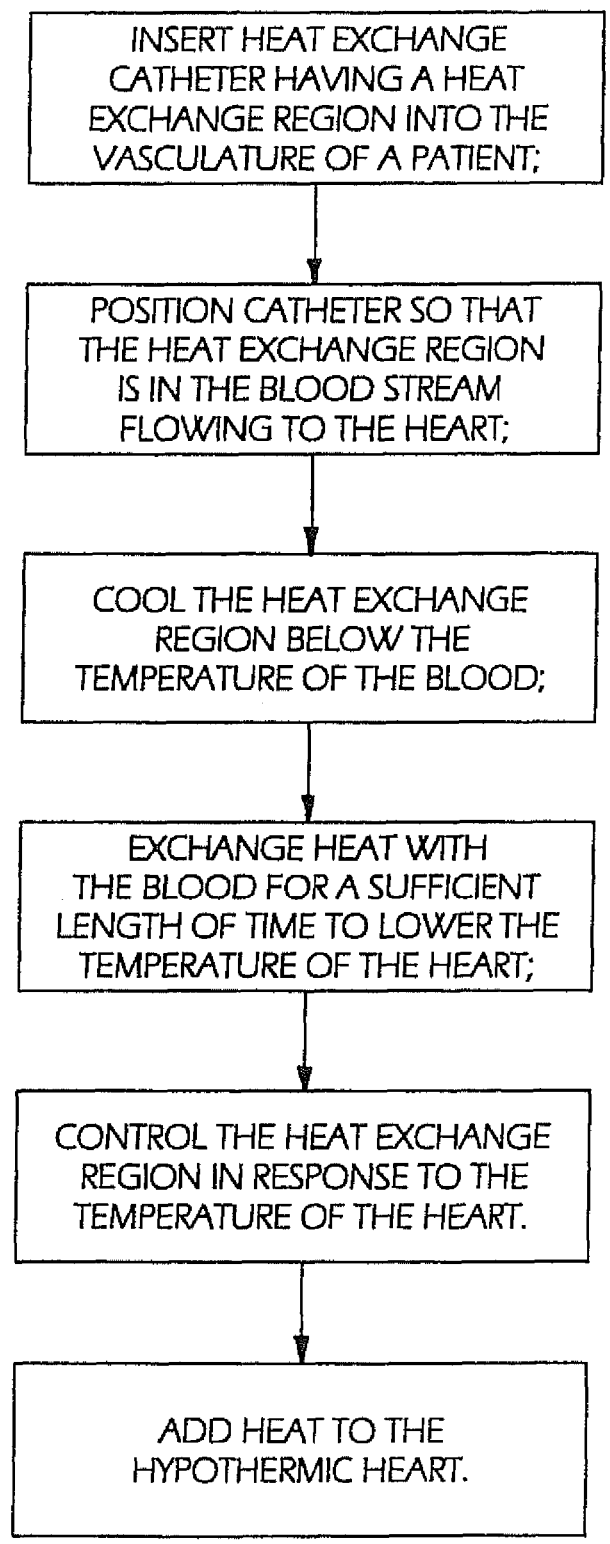
FIG. 21 is a flow chart depicting the steps of the method as described in the detailed description.

The method of the invention is described in the flow chart of FIG. 21. In Step 1, the heat exchange catheter is inserted into the vasculature of a patient. This is typically inserted percutaneously into the femoral vein, but may also be inserted into the internal jugular vein, or in any other suitable fashion depending on the circumstances. For example, if the patient is in surgery, insertion by a cut-down may be preferable. If access to the listed veins is not possible because the patient is aged or has other catheters or the like occupying the preferred locations, alternative locations are within the scope of the invention. Use of an insertion diameter of 8 French or less (3 F/mm) is generally preferable, but larger catheters are within the anticipated scope of the invention. Use of any of the cooling catheters described above is anticipated, as would be the use of any acceptable intravenous cooling catheter.

In step two, the catheter is advanced until the heat exchange region is in the blood stream flowing to the heart. This catheter placement is easily accomplished by those of skill in the art. It may be advanced using a guide wire, without a guide wire, using a guide catheter, or without a guiding catheter. It may be advanced using other well-known techniques as appropriate for the situation and the structure of the catheter, for example using bare wire or rapid exchange technique if applicable. It may be advanced from the femoral vein into the IVC, from an internal jugular insertion into the internal jugular vein into the SVC or the IVC, or if appropriate, even into the heart itself from either femoral or internal jugular insertion. Any location for the insertion and placement of the catheter that results in cooling of the blood directed to the heart is within the anticipated scope of this disclosure.

In step three, the heat exchange region is cooled below the temperature of the blood. The heat exchange region may be cooled to about 0° C., although it should not be cooled much below that temperature. The blood is largely water and is generally not damaged by contact with a surface that is as cold as 0° C. for the length of time that the blood is in contact with the heat exchange region, but with a surface much colder than that, blood in contact with the heat exchange region would freeze, possibly damaging the blood and decreasing the effectiveness of heat exchange. However, cooling below that temperature might be acceptable if an acceptable, safe and efficient method of cooling were employed, as long as it resulted in the cooling of the heart by means of cooling of the blood directed to the heart to reduce infarct suffered as a result of an ischemic event. The method described in greatest detail above of reducing the temperature of the heat exchange region was circulating cold saline through a balloon or hollow metallic element, or multiple heat exchange elements, to exchange heat with the blood through the surface of the heat exchange element, but other acceptable means of cooling the heat exchange region may be employed in practicing this invention.

The fourth step of the invention involves maintaining the exchanging of heat for a sufficient length of time to reduce the temperature of the heart. In the examples shown, about 240 watts of heat were being removed from the blood in the IVC to lower the temperature of the heart from 38° C. to about 33° C. in about 55 minutes. Depending on the desired level of hypothermia, the amount of blood flowing past the catheter, the number of watts of heat being removed from the blood by the heat exchange region, and similar variables, that rate of cooling may well be different and still be within the scope of this invention. It is generally the case that the cardiac temperature will be lowered to 35° C. or less to enjoy the benefits of mild hypothermia to reduce infarct, but depending on the individual situation, this may vary somewhat and still fall within the scope of this invention.

The application of hypothermia may be before the ischemic event, if an ischemic event is anticipated as is the case in surgery when it is known that the heart will be stopped for some period of time, or during balloon angioplasty when it is known that areas of the heart downstream of the balloon will be deprived of blood for some period of time. The hypothermia may be applied during the ischemia, as when it is applied during the two situations described above, whether or not it was applied before the ischemic event, or when it is applied to a heart attack victim when that victim presents. It may be applied after the ischemic event has occurred, as when it is applied to a heart attack victim soon after the ischemic event has occurred but after the ischemia has resolved and reperfusion has occurred. In all these cases and in combinations thereof, the application of mild hypothermia will generally be beneficial to prevent infarct from resulting from the ischemic event.

Step 5 involves controlling the heat exchange region in response to heart temperature. This generally involves monitoring a temperature such as rectal, tympanic, esophageal, cardiac or other temperature that may be used to determine the temperature of the heart, and controlling the heat exchange region in response to that measurement. The control of the heat exchange region may be in many forms. One form described in detail above was the control of the temperature of heat exchange fluid being circulated through a heat exchange balloon that comprised the heat exchange region. This could be done, for example, by controlling the temperature of an external heat exchanger that was in contact with a bag of saline, which saline was being circulated through the heat exchange balloon. However, if the heart temperature is determined by other factors, such as the length of time of cooling, the amount of heat transfer, or other physiological measurements, the control may be exercised based on these features.

The specific activities that may constitute control are many. Cooling may be stopped and heat added to the blood after the heart has reached a certain target temperature. Alternatively, the heat exchange region may be removed, or the heat exchange region may be returned to normothermia. In a more elegant type of control, a target temperature may be pre-selected and the amount of heat added or removed from the blood may be adjusted so that the cardiac temperature achieves the target temperature and stays at the target temperature for some pre-selected length of time, and then may warm or cool toward a second pre-selected temperature that may be normothermia, or the like. The nature of the control in response to the temperature of the heart may vary greatly and still be within the scope of this invention.

Step six, optional but sometimes a step practiced in the method, is to add heat to the hypothermic heart.

Although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

What is claimed is:

1. A method for deterring myocardial damage in a patient who is suffering from a heart attack, said method comprising the steps of:
   (A) inserting a heat exchange catheter having a heat exchanger with a helical heat exchange surface into the vena cava of the patient;
   (B) circulating cooled heat exchange fluid through the heat exchanger to lower the patient's body temperature to 35 degrees C. or below; and, thereafter,
   (C) performing a procedure to restore blood flow to an ischemic area of the patient's myocardium; and, thereafter;
   (D) rewarming the patient's body to normothermia;
   wherein heat exchange fluid flows through the heat exchanger in a direction that is opposite the direction in which blood flows past the heat exchanger.

2. A method according to claim 1 wherein the helical heat exchange surface comprises helical fin formed on the heat exchanger.

3. A method according to claim 1 wherein the helical heat exchange surface comprises a helical heat exchange balloon.

4. A method according to claim 1 wherein the patient's body temperature is determined by placement of a temperature sensor in the patient's body.

5. A method according to claim 4 wherein the temperature sensor is placed in the patient's rectum.

6. A method according to claim 4 wherein the temperature sensor is placed in the patient's esophagus.

7. A method according to claim 4 wherein the temperature sensor is placed in the patient's ear to sense temperature at the tympanic membrane.

8. A method according to claim 4 wherein the temperature sensor is placed in the patient's heart.

9. A method according to claim 8 wherein the temperature sensor is placed in the left atrium of the patient's heart.

10. A method according to claim 8 wherein the temperature sensor is placed in the left ventricle of the patient's heat.

11. A method according to claim 4 wherein the temperature sensor is located on the heat exchange catheter.

12. A method according to claim 1 wherein the procedure comprises an angioplasty procedure.

13. A method according to claim 1 wherein the procedure comprises a stenting procedure.

14. A method according to claim 1 wherein the procedure comprises cardiac surgery.

15. A method for deterring myocardial damage in a patient who is suffering from a heart attack, said method comprising the steps of:
   (A) inserting a heat exchange catheter having a heat exchanger with a helical heat exchange surface into the vena cava of the patient;
   (B) circulating cooled heat exchange fluid through the heat exchanger to lower the patient's body temperature to 35 degrees C. or below; and, thereafter,
   (C) performing a procedure to restore blood flow to an ischemic area of the patient's myocardium; and, thereafter;
   (D) rewarming the patient's body to normothermia;
   wherein a temperature sensor is placed in the patient's heart.

16. A method according to claim 15 wherein the temperature sensor is placed in the left atrium of the patient's heart.

17. A method according to claim 15 wherein the temperature sensor is placed in the left ventricle of the patient's heat.

18. A method according to claim 17 wherein the temperature sensor is located on the heat exchange catheter.

19. A method according to claim 15 wherein the procedure comprises an angioplasty procedure.

20. A method according to claim 15 wherein the procedure comprises a stenting procedure.

21. A method according to claim 15 wherein the procedure comprises cardiac surgery.

22. A method according to claim 15 wherein heat exchange fluid flows through the heat exchanger in a direction that is opposite the direction in which blood flows past the heat exchanger.

23. A method according to claim 15 wherein the helical heat exchange surface comprises a helical fins formed on the heat exchanger.

24. A method according to claim 15 wherein the helical heat exchange surface comprises a helical heat exchange balloon.

* * * * *